United States Patent [19]

Tseng et al.

[11] Patent Number: 4,847,256
[45] Date of Patent: Jul. 11, 1989

[54] 4,5-DIHYDRO AND 4,5,6,7-TETRAHYDROPYRAZOLO(1,5-A)-PYRIMIDINES

[75] Inventors: Shin S. Tseng, Bridgewater, N.J.; John P. Dusza, Nanuet, N.Y.; Joseph W. Epstein, Monroe, N.Y.

[73] Assignee: American Cyanamid Company, Stamford, Conn.

[21] Appl. No.: 919,730

[22] Filed: Oct. 16, 1986

[51] Int. Cl.$^4$ .................. C07D 471/04; A61K 31/505
[52] U.S. Cl. .................... 514/258; 544/281; 546/328; 548/375; 548/377; 564/194; 564/342; 564/345; 558/440
[58] Field of Search ............... 514/258; 544/281, 282

[56] References Cited

U.S. PATENT DOCUMENTS

| | | | |
|---|---|---|---|
| 4,521,422 | 6/1985 | Dusza et al. | 514/258 |
| 4,576,943 | 3/1986 | Tomcufcik et al. | 544/281 |
| 4,654,347 | 3/1987 | Dusza et al. | 544/281 |

FOREIGN PATENT DOCUMENTS 129847 1/1985 European Pat. Off. ............ 544/281

*Primary Examiner*—Anton H. Sutto
*Assistant Examiner*—E. Bernhardt
*Attorney, Agent, or Firm*—H. G. Jackson

[57] ABSTRACT

Novel compounds having the following structural formula:

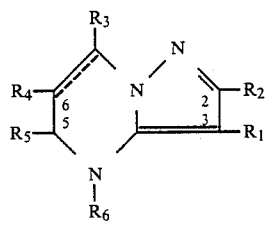

Ia or Ib wherein - - - may represent the presence of a double bond between the $C_6$ and $C_7$ position, Ia, or the absence of a double bond between the $C_6$ and $C_7$ position, Ib; $R_1$ is selected from the group consisting essentially of hydrogen, bromo, chloro, carbamoyl, carboxyl, carboxyalkoxyl where alkoxyl is ($C_1$-$C_3$), cyano, —CO—$CF_3$, COONa,

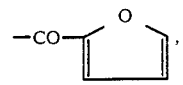

—CO—C(CH$_3$)$_3$, and

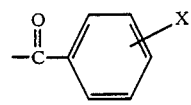

where X is hydrogen, cyano, halogen and nitro; $R_2$, $R_4$ and $R_5$ may be hydrogen and lower alkyl ($C_1$-$C_3$); $R_3$ is hydrogen, alkyl ($C_1$-$C_3$),

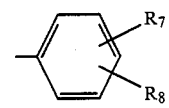

where $R_7$ and $R_8$ may be the same or different and are selected from the group consisting essentially of hydrogen, halogen, alkyl ($C_1$-$C_3$), nitro, alkoxy ($C_1$-$C_3$), trifluoro-methyl, acetylamino or N-alkylacetylamino where alkyl is ($C_1$-$C_3$), and $R_3$ may also be selected from a monovalent radical selected from the class consisting essentially of 3-thienyl, 2-pyridinyl, 3-pyridinyl and 4-pyridinyl, either of said pyridinyl radicals being optionally substituted with an alkyl radical $R_9$, where alkyl is ($C_1$-$C_4$), and the structures of the monovalent 2-pyridinyl, 3-pyridinyl and 4-pyridinyl moieties are depicted respectively as:

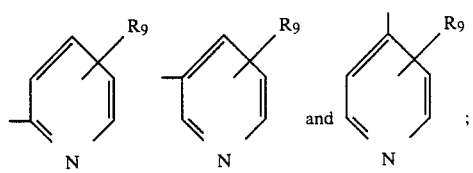

$R_6$ is hydrogen or alkyl-($C_1$-$C_3$); pharmaceutical compositions of matter containing the above-defined compounds; methods for using the compounds as anxiolytic agents, antihypertensive agents or antidepressant agents in mammals; processes for the preparation of the compounds.

15 Claims, No Drawings

4,5-DIHYDRO AND 4,5,6,7-TETRAHYDROPYRAZOLO(1,5-A)-PYRIMIDINES

BRIEF SUMMARY OF THE INVENTION

The present invention relates to new organic compounds and more particularly is concerned with novel 4,5-dihydro and 4,5,6,7-tetrahydropyrazolo[1,5-a]pyrimidines useful as anxiolytic agents, antihypertensive agents or antidepressant agents in mammals, or as intermediates. The compounds of the present invention may be represented by the following structural formula:

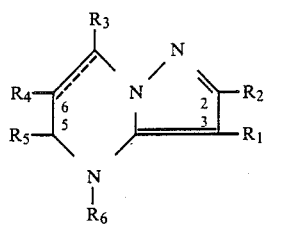

Ia or Ib wherein—may represent the presence of a double bond between the $C_6$ and $C_7$ position, Ia, or the absence of a double bond between the $C_6$ and $C_7$ position, Ib; $R_1$ is selected from the group consisting essentially of hydrogen, bromo, chloro, carbamoyl, carboxyl, carboxyalkoxyl where alkoxyl is $(C_1-C_3)$, cyano, —CO—CF$_3$, COONa,

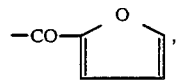

—CO—C(CH$_3$)$_3$, and

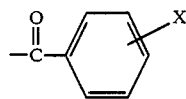

where X is hydrogen, cyano, halogen and nitro; $R_2$, $R_4$ and $R_5$ may be hydrogen and lower alkyl$(C_1-C_3)$; $R_3$ is hydrogen, alkyl$(C_1-C_3)$,

where $R_7$ and $R_8$ may be the same or different and are selected from the group consisting essentially of hydrogen, halogen, alkyl$(C_1-C_3)$, nitro, alkoxy$(C_1-C_3)$, trifluoromethyl, acetylamino or N-alkylacetylamino where alkyl is $(C_1-C_3)$, and $R_3$ may also be selected from a monovalent radical selected from the class consisting essentially of 3-thienyl, 2-pyridinyl, 3-pyridinyl and 4-pyridinyl, either of said pyridinyl radicals being optionally substituted with an alkyl radical $R_9$, where alkyl is $(C_1-C_4)$, and the structures of the monovalent 2-pyridinyl, 3-pyridinyl and 4-pyridinyl moieties are depicted respectively as:

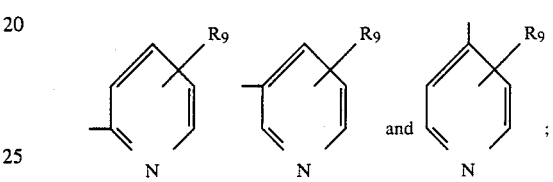

$R_6$ is hydrogen or alkyl$(C_1-C_3)$.

The present invention also includes novel compositions of matter containing the above-defined compounds which are useful as anxiolytic agents, antihypertensive agents or antidepressant agents in mammals and the methods for meliorating anxiety, treating hypertension and alleviating depression in mammals therewith.

The invention also comprises processes for the preparation of compounds within the scope of formulae Ia and Ib.

DETAILED DESCRIPTION OF THE INVENTION

The novel compounds of the present invention are obtainable as colorless to yellow crystalline materials having characteristic melting points and absorption spectra. They are generally soluble in organic solvents such as lower alkanols, chloroform, tetrahydrofuran, N,N-dimethyl-formamide, dichloromethane, acetone and the like but are generally insoluble in water.

The novel 4,5-dihydro and 4,5,6,7-tetrahydropyrazolo [1,5-a]pyrimidines of the present invention may be readily prepared as set forth in the following reaction schemes:

SCHEME 1

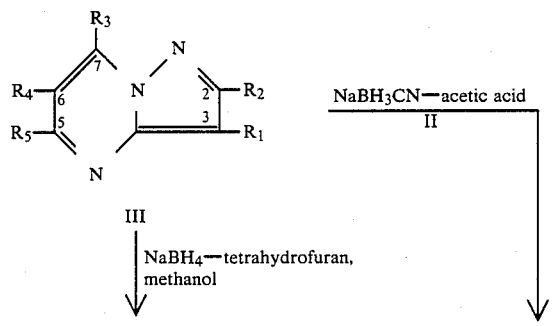

SCHEME 1

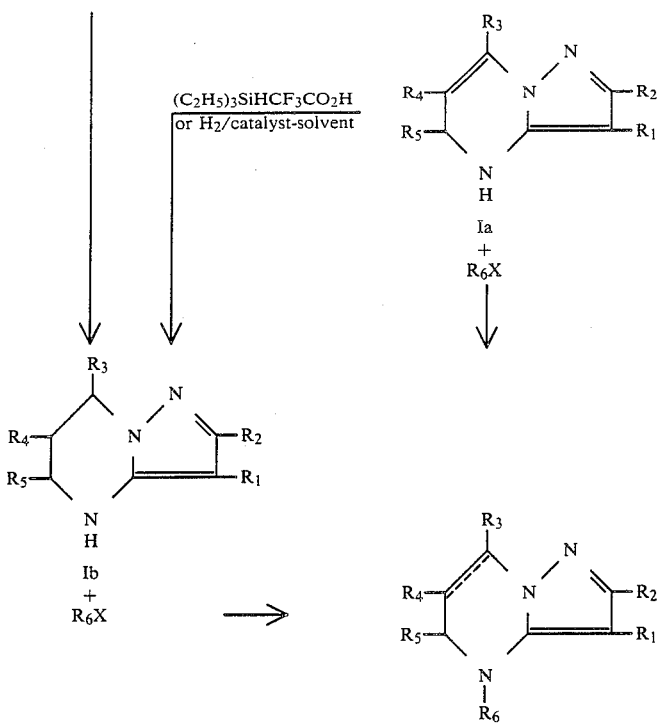

wherein $R_1$, $R_2$, $R_3$, $R_4$, $R_5$ and $R_6$ are as hereinabove defined and X is halogen.

As shown hereinabove (scheme 1) a pyrazolo[1,5-a]pyrimidine III, with a hydrogen, phenyl, substituted phenyl, or heteroaryl group in the C-7 position and an electron-withdrawing group in the C-3 position is reacted with sodium cyanoborohydride II by stirring in glacial acetic acid under nitrogen in an ice bath for approximately one hour, then at room temperature for from 1-12 hours. The resulting precipitate is collected and washed with water, then is dissolved in an inert solvent such as dichloromethane or acetonitrile and the like and washed with saturated sodium bicarbonate. Separation and evaporation of the organic phase gives the crude dihydro product Ia which is recrystallized from a solvent such as isopropyl alcohol or acetonitrile and the like or from a mixture of solvents such as ether-hexane, chloroform-methanol or N,N-dimethylformamide-acetonitrile and the like.

The dihydro product Ia is reduced with triethylsilane in trifluoroacetic acid at 60° C. for 1-24 hours according to the procedure of Lanzilotti, et al., J. Org. Chem., 44, 4809 (1979). The reaction mixture at ambient temperature is made slightly basic (pH 9) with aqueous potassium hydroxide to precipitate the product Ib which is then isolated and purified by crystallization or chromatography.

The reaction of the dihydro product Ia or the tetrahydro product Ib, when dissolved in a solvent such as N,N-dimethylformamide and the like, with an alkylating agent such as methyl iodide or dimethyl sulfate and the like in the presence of sodium hydride provides the corresponding product where $R_6$ is alkyl.

The pyrazolo[1,5-a]pyrimidines III are disclosed in U.S. Pat. Nos. 4,178,449; 4,236,005 and 4,281,000 and in pending application, Ser. No. 612,812, filed May 24, 1984 and allowed on Jan. 10, 1985. They are prepared by condensation of 3-aminopyrazoles and substituted 3-aminopyrazoles with 1,3-dicarbonyl compounds as described in J. Med. Chem., 18, 645 (1974); J. Med. Chem., 18, 460 (1975); J. Med. Chem., 20, 386 (1977; Synthesis, 673 (1982); and references contained therein.

The 7-aryl and 7-heteroaryl[1,5-a]pyrimidines which contain a 3-aroyl group, are synthesized by condensation of 1-aryl or 1-heteroaryl-1,3-dicarbonyl compounds with 3-amino-4-aroylpyrazoles.

It has been found that the use of sodium cyanoborohydride in acetic acid offers a simple, convenient, regioselective means for the reduction of pyrazolo[1,5-a]pyrimidines and derivatives thereof, bearing functional groups such as halogens, nitriles, amides, amidines, esters, carboxylic acids and aryl ketones without reducing these groups and providing the final products in higher yield then obtained with other reducing agents. In fact, certain of the above described functional groups are known to be affected by the use of other reducing agents, with mixtures of products being formed which require the employment of time consuming separation techniques to obtain the desired product.

In rare instances the reduction of pyrazolo[1,5-a]pyrimidine derivatives with sodium cyanoborohydride in glacial acetic acid results in complete reduction to the tetrahydro form, whereas predominately the reduction procedure provides the dihydro product.

Another effective means for the reduction of pyrazolo[1,5-a]pyrimidines is concerned with the utilization of sodium borohydride in glacial acetic acid. This method although effective does not provide yields commensurate with those obtained by the use of sodium cyanoborohydride. This difference could be due to the fact that sodium cyanoborohydride is more stable in glacial acetic acid then is sodium borohydride. It has also been discovered that when sodium borohydride is reacted with a pyrazolo[1,5-a]pyrimidine derivative such as 7-(4-chlorophenyl)-5-methylpyrazolo[1,5-a]pyrimidine-3-carbonitrile or 7-(3-chlorophenyl)-5-methylpyrazolo[1,5-a]pyrimidine-3-carbonitrile in tetrahydrofuran:methanol (1:1) by stirring at room temperature for 24 hours or at 55° C. for six hours the corresponding tetrahydro compound is obtained.

Still another means for the reduction of pyrazolo[1,5-a]pyrimidines or further reduction of 4,5-dihydropyrazolo[1,5-a]pyrimidines to the 4,5,6,7-tetrahydro form resides with the catalytic hydrogenation of the compound by shaking in a suitable apparatus, such as a Parr shaker, with a solvent such as ethyl acetate, N,N-dimethylformamide, or the like in the presence of a catalyst such as 10% palladium on carbon under an initial hydrogen pressure of from 5–30 lbs. until the uptake of hydrogen is complete followed by separation and purification of the reduction product by conventional means.

Certain of the novel compounds of the present invention possess central nervous system activity at nontoxic doses and as such are useful as anxiolytic agents. They produce certain responses in standard tests with laboratory animals which are known to correlate well with relief of anxiety in human beings. The compounds, when tested pharmacologically, are found to have a desirable wide spread between doses producing anxiolytic activity and toxic symptoms.

The antianxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle containing 0.5% v/v polyethylene glycol and one drop of polysorbate 80, or distilled water and one drop of polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", pp. 237–288 (Eds. R. R. Rech and K. E. Moore, Raven Press, New York, 1971) that there is a high degree of correlation between antagonism of pentylenetetrazole seizures in rats and antianxiety effects in higher warm-blooded animals. The results of this in vivo test on representative compounds of the present invention are shown in Table I.

TABLE I

| Protection Against Clonic Seizures Caused By Pentylenetetrazole In Rats | | |
|---|---|---|
| Compound | Dose (mg/kg) | % of Rats Protected |
| 4,5-Dihydro-7-[3-(trifluoromethyl)-phenyl]pyrazolo[1,5-a]pyrimidine-3-carbonitrile | 25 | 100 50 |
| 4,5-Dihydro-7-phenylpyrazolo[1,5-a]pyrimidine-3-carboxamide | 25 | 50 |
| [4,5-Dihydro-7-[3-(trifluoromethyl)-phenyl]pyrazolo[1,5-a]pyrimidin-3-yl]- | 25 | 75 |

TABLE I-continued

| Protection Against Clonic Seizures Caused By Pentylenetetrazole In Rats | | |
|---|---|---|
| Compound | Dose (mg/kg) | % of Rats Protected |
| phenylmethanone | | |

Another test used to assess antianxiety effects is a non-conditioned passive avoidance procedure described by J. R. Vogel, B. Beer and D. E. Clody, "A Simple and Reliable Conflict Procedure for Testing Antianxiety Agents", Psychopharmacologia, 21:1–7 (1971). A conflict situation is induced in rats by a modification of this method.

Groups of 8 naive, Wistar strain male rats weighing 200–240 g each were deprived of water for 48 hours. The test compounds were administered in single or graded, oral doses, suspended in 2% starch with 5% polyethylene glycol in distilled water and one drop of polysorbate 80. Control animals received the vehicle alone. At 60 minutes each rat was placed in an individual clear plastic chamber. Tap water was available ad libitum from a nipple located in a black box off the main chamber. A 0.7 milliampere AC shocking current was established between the stainless steel grid floor and the tap. After 20 licks of non-shocked drinking, a 2 second shocking current was administered to the rat. This ratio of 20 licks of non-shocked drinking followed by a 2 second shock was continued for a total of 3 minutes. The number of shocks taken by each rat during the 3 minute interval was recorded and compared to a control group. The test compounds are considered active if the number of shocks received by the test group is significantly higher than the control group by the Mann-Whitney U test. That is, the test compounds are considered active if they result in the treated rat taking slightly more than double the number of shocks that the untreated rat will take. Results of this in vivo test on a representative compound of the present invention are given in Table II.

TABLE II

| Conflict Procedure In Rats | | |
|---|---|---|
| Compound | Dose (mg/kg) | Result (no. of shocks per 3 min.) |
| [4,5-Dihydro-7-[3-(trifluoromethyl)phenyl]pyrazolo[1,5-a]pyrimidin-3-yl]phenylmethanone | 25 | 19.1 |
| 4,5-Dihydro-4-methyl-7-[3-(trifluoromethyl)phenyl]pyrazolo[1,5-a]pyrimidine-3-carbonitrile | 25 | 19.0 |

Still another test utilized for the determination of anxiolytic activity is the measurement of the ability of a test compound to inhibit the binding of tritiated benzodiazepines to brain-specific receptors of mammals. A modification of the method described by R. F. Squires, et al., Nature, 266, No. 21:732 (April, 1977) and H. Mohler, et al., Science, 198:849 (1977) was employed.

Male albino rats (Wistar strain, weighing 150–200 g each) were used. The test compounds were solubilized in dimethylformamide, acetic acid, ethanol or hydrochloric acid.

Whole cortex of rats was homogenized gently in 20 volumes of ice-cold 0.32 M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$ C.) until time of use. Frozen $P_2$ preparations were thawed and resuspended in four times the original homogenizing volume at time of assay.

The binding assay consisted of 300 $\mu$l of the $P_2$-fraction suspension (0.2–0.4 mg protein), 100 $\mu$l of test drug and 100 $\mu$l of $^3$H-diazepam (1.5 nM, final concentration) or $^3$H-flunitrazepam (1.0 nM, final concentration) which was added to 1.5 ml of 50 nM Tris.HCl (pH 7.4). Nonspecific binding controls and total binding controls received 100 $\mu$l of diazepam (3 $\mu$M final concentration) and 100 $\mu$l of deionized water, respectively, in place of the test compound. Incubation for 30 minutes proceeded in ice and was terminated by filtration, under vacuum, through glass fiber filters. The filters were washed twice with 5 ml of ice-cold 50 mM Tris.HCl (pH 7.4) and placed in scintillation vials. After drying at 50°–60° C. for 30 minutes, 10 ml of diluent was added and the radioactivity determined in a scintillation counter.

Inhibition of binding was calculated by the difference between total binding and binding in the presence of test compound, divided by the total binding, $\times 100$. Physiological activity can be shown by a test compound that inhibits $^3$H-benzodiazepine binding by 12% or more. Such in vitro activity is biologically relevant when the test compound also demonstrates statistically significant anxiolytic activity through in vivo studies.

The result of this in vitro test on a representative compound of this invention is given in Table III.

TABLE III

| Inhibition of the Binding of $^3$H Benzodiazepine to Brain-Specific Receptors of Rats | |
|---|---|
| Compound | % Inhibition |
| 4,5-Dihydro-7-[3-(trifluoromethyl)phenyl]-pyrazolo[1,5-a]pyrimidine-3-carbonitrile | 15 |
| 4,5-Dihydro-7-phenylpyrazolo[1,5-a]pyrimidine-3-carbonitrile | 20 |
| 4,5-Dihydro-7-phenylpyrazolo[1,5-a]pyrimidine-3-carboxylic acid, ethyl ester | 54 |
| 4,5-Dihydro-7-[3-(trifluoromethyl)phenyl]-pyrazolo[1,5-a]pyrimidine-3-carboxylic acid, ethyl ester | 90 |
| [4,5-Dihydro-7-[3-(trifluoromethyl)phenyl]-pyrazolo[1,5-a]pyrimidin-3-yl]phenylmethanone | 76 |
| Phenyl[4,5,6,7-tetrahydro-7-(4-pyridinyl)-pyrazlo[1,5-a]pyrimidin-3-yl]methanone | 22 |
| 4,5-Dihydro-4-methyl-7-[3-(trifluoromethyl)-phenyl]pyrazolo[1,5-a]pyrimidine-3-carbonitrile | 12 |
| 2,2-Dimethyl-1-(4,5,6,7-tetrahydropyrazolo-[1,5-a]pyrimidin-3-yl)-1-propanone | 28 |
| 7-(3-Fluorophenyl)-4,5-dihydropyrazolo-[1,5-a]pyrimidine-3-carboxamide | 39 |
| 3-Chloro-4,5-dihydro-7-[3-(trifluoromethyl)-phenyl]pyrazolo[1,5-a]pyrimidine | 63 |
| 4,5-Dihydro-7-[3-(trifluoromethyl)phenyl]-pyrazolo[1,5-a]pyrimidine | 48 |
| 7-(3,4-Dichlorophenyl)-4,5-dihydropyrazolo-[1,5-a]pyrimidine-3-carbonitrile | 12 |

Certain of the novel compounds of the present invention are active hypotensive agents at nontoxic doses when administered to mammals. These compounds were tested for hypotensive activity by the method of P. S. Chan and D. W. Poorvin, Clinical and Experimental Hypertension, 1 (6), 817–830 (1979). Male, 16 week old, spontaneously hypertensive rats of the Okamoto strain having an average mean arterial blood pressure of 160±1.5 mm of mercury are used in the test. One to three rats are used per test compound. A rat is dosed by gavage with a test compound, suspended in 2% preboiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention appear below in Table IV.

TABLE IV

| Reduction of Mean Arterial Blood Pressure in Spontaneously Hypertensive Rats | |
|---|---|
| Compound | MABP/mm Hg (no. of rats) |
| 4,5-Dihydro-7-[3-(trifluoromethyl)phenyl]-pyrazolo[1,5-a]pyrimidine-3-carboxamide | 108(1) |
| 7-(2,5-Dichlorophenyl)-4,5-dihydro-2-methylpyrazolo[1,5-a]pyrimidine-3-carboxamide | 95(1) |
| [4,5-Dihydro-7-[3-(trifluoromethyl)phenyl]-pyrazolo[1,5-a]pyrimidin-3-yl]phenylmethanone | 122(2) |
| Phenyl[4,5,6,7-tetrahydro-7-(4-pyridinyl)-pyrazolo[1,5-a]pyrimidin-3-yl]methanone | 125(1) |
| 4,5,6,7-Tetrahydro-7-[3-(trifluoromethyl)-phenyl]pyrazolo[1,5-a]pyrimidine-3-carbonitrile | 128(1) |
| 4,5,6,7-Tetrahydropyrazolo[1,5-a]pyrimidine-3-carboxamide | 137(1) |
| 2,2-Dimethyl-1-(4,5,6,7-tetrahydropyrazolo-[1,5-a]pyrimidin-3-yl)-1-propanone | 114(1) |

The compounds of this invention are active as antidepressant agents in warm-blooded animals as evidenced by their results when tested in the Stress Induced Immobility Test. In this test, rats were confined on a warm (44.5° C.), but aversive, surface for 15 minutes. After 5–6 minutes, control rats began to show episodes of behavior where they remained flat and immobile for periods of time. The total duration of this behavior was timed. The average duration of immobility in the control rats was 200 seconds. The test compounds were administered intraperitoneally at 25 mg/kg of body weight. A compound was considered active if the maximum duration time was <100 seconds (less than 50% of the control value) in more than 50% of the rats.

The results of this test on representative compounds of the present invention appear in Table V.

TABLE V

| Stress Induced Immobility Test | | |
|---|---|---|
| Compound | No. of Rats Responding No. of Rats Tested | Mean Duration (Seconds) |
| 4,5-Dihydro-6-methyl-7-[3-(trifluoromethyl)-phenyl]pyrazolo[1,5-a]-pyrimidine-3-carbonitrile | 4/5 | 55.0 |
| 7-(3-Chlorophenyl)-4,5,6,7-tetrahydro-5-methylpyrazolo[1,5-a]-pyrimidine-3-carbonitrile | 4/5 | 75.4 |
| 7-(3-Chlorophenyl)-4,5-dihydro-6-methyl- | 2/3 | 66.7 |

TABLE V-continued

Stress Induced Immobility Test

| Compound | No. of Rats Responding No. of Rats Tested | Mean Duration (Seconds) |
|---|---|---|
| pyrazolo[1,5-a]pyrimidine-3-carbonitrile | | |
| 7-(4-Chlorophenyl)-4,5,6,7-tetrahydro-5-methylpyrazolo[1,5-a]-pyrimidine-3-carbonitrile | 3/3 | 4.7 |

The novel compounds of the present invention which are effective for meliorating anxiety in warm-blooded animals are administered in amounts ranging from about 0.1 mg to about 35.0 mg/kg of body weight per day preferred dosage regimen for optimum results would be from about 0.5 mg to about 20.0 mg/kg of body weight per day and such dosage units are employed that a total of from about 35 mg to about 1.4 g of the active compound for a subject of about 70 kg of body weight are administered in a 24 hour period.

Certain of the novel compounds of the present invention have been found to be highly useful for lowering elevated blood pressure or alleviating depression in mammals when administered in amounts ranging from about 2.5 mg to about 100 mg/kg of body weight per day. A preferred dosage regimen for optimum results would be from about 50 mg to about 750 mg per dose. Such dosage units are employed that a total of from about 200 mg to about 3.0 g of the active compound for a subject of about 70 kg of body weight are administered in a 24 hour period.

The dosage regimen for the above-described utilities may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier. They may be enclosed in hard or soft shell gelatin capsules or compressed into tablets. They also may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as sodium lauryl sulfate or an emulsifier or stabilizer such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The invention will be described in greater detail in conjunction with the following non-limiting examples.

EXAMPLE 1

7-[3-(Trifluoromethyl)phenyl]pyrazolo[1,5-a]-pyrimidine-3-carboxamide

A mixture of 3.0 g of 7-(α,α,α-trifluoro-m-tolyl)-pyrazolo[1,5-a]pyrimidine-3-carbonitrile (prepared as described in U.S. Pat. No. 4,236,005) and 150 ml of concentrated sulfuric acid was stirred at room temperature for 4 hours. The solution was then carefully poured into ice water with stirring. The white precipitate formed was collected, washed with water and then with saturated sodium bicarbonate until it was neutral. The solid was heated with one liter of isopropyl alcohol and filtered. The white solid was dried in vacuo and gave the product of the example as a colorless solid, mp 256°–258° C.

EXAMPLE 2

7-(2,5-Dichlorophenyl)-2-methylpyrazolo[1,5-a]pyrimidine-3-carboxamide

A mixture of 31.0 g of 2',5'-dichloroacetophenone and 25 ml of N,N-dimethylformamide dimethyl acetal was heated on a steam bath for 6 hours, then evaporated to dryness in vacuo. The residue was slurried with hexane, filtered, and gave 35.3 g of 2',5'-dichloro-3-dimethylaminoacrylophenone as orange crystals, mp 83°–85° C.

A mixture of 12.2 g of 3-amino-4-cyano-5-methylpyrazole and 24.4 g of 2',5'-dichloro-3-dimethylaminoacrylophenone in 250 ml of glacial acetic acid was heated on a steam bath for 4 hours. The mixture was cooled and filtered and gave 21.28 g of 7-(2,5-dichlorophenyl)-2-methylpyrazolo[1,5-a]pyrimidine-3-carbonitrile as off-white crystals.

The preceding product 21.28 g was dissolved in concentrated sulfuric acid and stirred for 5 hours. The solution was carefully poured onto ice. The precipitate which formed was collected by filtration, washed with water and air dried to give the product of the example as colorless crystals, mp 234°–236° C.

Additional pyrazolo[1,5-a]pyrimidine-3-carboxamides which were prepared from the corresponding pyrazolo[1,5-a]pyrimidine-3-carbonitriles in the manner described in Example 1 are listed in Table VI.

The pyrazolo[1,5-a]pyrimidine-3-carbonitriles were prepared by the procedures described in U.S. Pat. Nos. 4,178,449, 4,236,005 and 4,281,000 by reacting the appropriate 3-(dimethylamino)acrylophenone intermediate with an appropriately substituted 3-aminopyrazole-4-carbonitrile.

TABLE VI

Pyrazolo[1,5-a]1,5-a]pyrimidine-3-carboxamides

| Ex. | Compound | $R_2$ | $R_3$ | MP °C. |
|---|---|---|---|---|
| 3 | 7-Phenylpyrazolo[1,5-a]pyrimidine-3-carboxamide | H | phenyl | 236–238.5 |
| 4 | 2-Methyl-7-phenylpyrazolo[1,5-a]pyrimidine-3-carboxamide | $CH_3$ | phenyl | 233–235 |
| 5 | 7-(3-Pyridinyl)pyrazolo[1,5-a]pyrimidine-3-carboxamide | H | 3-pyridinyl | 285–286 |
| 6 | 7-(4-Pyridinyl)pyrazolo[1,5-a]pyrimidine-3-carboxamide | H | 4-pyridinyl | 394–396 |
| 7 | 7-(3-Fluorophenyl)pyrazolo[1,5-a]pyrimidine-3-carboxamide | H | 3-fluorophenyl | 247–249 |

EXAMPLE 8

Phenyl[7-[3-(trifluoromethyl)phenyl]pyrazolo[1,5-a]pyrimidin-3-yl]methanone

A reaction mixture of 1.87 g of (3-amino-1H-pyrazol-4-yl)phenyl-methanone and 2.43 g of 3-dimethylamino-1-[3-(trifluoromethyl)phenyl]-2-propen-1-one in 25 ml of glacial acetic acid was refluxed for 6 hours and then the solvent was removed in vacuo giving a crystalline residue. This residue was partitioned between saturated aqueous sodium bicarbonate and dichloromethane. The organic layer was dried with anhydrous sodium sulfate and then passed through a short pad of hydrous magnesium silicate. The addition of hexane to the refluxing eluate induced crystallization. After cooling, the desired product was collected as crystals, mp 148°–150° C.

EXAMPLE 9

Phenyl[7-(4-pyridinyl)pyrazolo[1,5-a]pyrimidin-3-yl]methanone

Following the general procedure of Example 8 and reacting (3-amino-1H-pyrazol-4-yl)phenyl-methanone with 3-dimethylamino-1-(4-pyridinyl)-2-propen-1-one gave the desired product, mp 185°–186° C.

EXAMPLE 10

7-(3-Chlorophenyl)pyrazolo[1,5-a]pyrimidine-3-carbonitrile

A mixture of 50.0 g of 3'-chloro-3-dimethylaminoacrylophenone, 25.0 g of 3-aminopyrazole-4-carbonitrile and 500 ml of glacial acetic acid was heated at reflux for 2 hours. The mixture went into solution upon heating and a precipitate formed after one hour of refluxing. The reaction mixture was filtered and the crystals collected were triturated with saturated aqueous sodium bicarbonate, filtered and washed with water and then dried to give 49.0 g of the product of the example as colorless crystals, mp 238°–240° C.

EXAMPLE 11

7-(3-Nitrophenyl)pyrazolo[1,5-a]pyrimidine-3-carbonitrile

A mixture of 24.4 g of 3-dimethylamino-3'-nitroacrylophenone, 13.0 g of 3-aminopyrazole-4-carbonitrile and 120 ml of glacial acetic acid was heated at reflux for 7 hours, then was stirred at room temperature for 16 hours. The precipitate was collected, triturated with saturated aqueous sodium bicarbonate, filtered and washed with water. The solid was then triturated with acetonitrile, filtered and dried and gave the desired product, mp 244°–246° C.

EXAMPLE 12

N-[3-(3-Cyanopyrazolo[1,5-a]pyrimidin-7-yl)phenyl]-N-methylacetamide

A mixture of 540 mg of 3-aminopyrazole-4-carbonitrile, 1.23 g of N-[3-[3-(dimethylamino)-1-oxo-2-propenyl]phenyl]-N-methylacetamide and 50 ml of glacial acetic acid was heated at reflux for 8 hours then the solvent was removed. The residue was partitioned between saturated aqueous sodium bicarbonate and dichloromethane. The organic layer was separated, dried, passed through a pad of hydrous magnesium silicate and hexane was added to the refluxing filtrate to crystallize the product. The mixture was cooled and the solid collected, giving the desired product, mp 195°–197° C.

EXAMPLE 13

N-[3-(3-Cyanopyrazolo[1,5-a]pyrimidin-7-yl)phenyl]acetamide

A mixture of 6.0 g of 3-aminopyrazole-4-carbonitrile, 13.0 g of N-[3-[3-(dimethylamino)-1-oxo-2-propenyl]phenyl]acetamide and 100 ml of glacial acetic acid was heated at reflux for 4 hours. On standing at room temperature a precipitate formed. The precipitate was isolated, washed with hexane, then ether and dried. The solid was recrystallized from acetonitrile-N,N-dimethylformamide and gave the product of the example, mp 252°–254° C.

EXAMPLE 14

7-(3-Chlorophenyl)-5-methylpyrazolo[1,5-a]pyrimidine-3-carbonitrile

A mixture of 50.0 g of 3-chloroacetophenone and 75.0 ml of N,N-dimethylacetamide dimethyl acetal was stirred and heated at reflux for 16 hours. The mixture was evaporated in vacuo to give an oil. The oil was triturated with hexane while cooling in an ice bath. Scratching induced crystal formation. The crystals were collected by filtration and gave 60.2 g of 1-(3-chlorophenyl)-N-(dimethylamino)-2-buten-1-one as red crystals, mp 38°–40° C.

A mixture of 30.0 g of the preceding compound, 14.48 g of 3-aminopyrazole-4-carbonitrile and 200 ml of glacial acetic acid was stirred and heated at reflux for 2 hours, with formation of a solid. The mixture was allowed to stand at room temperature for 16 hours, then was filtered. The white crystalline precipitate was triturated with sodium bicarbonate to neutralize, then was filtered. The crystals were copiously washed with water, then dried to give the product of the example as white crystals, mp 218°–220 °C.

EXAMPLE 15

7-(4-Chlorophenyl)-5-methylpyrazolo[1,5-a]pyrimidine-3-carbonitrile

A mixture of 25.0 g of 4-chloroacetophenone and 40 ml of N,N-dimethylacetamide dimethyl acetal was stirred and heated at reflux for 3 hours. The mixture was evaporated in vacuo to give a red solid. The solid was triturated with n-hexane and filtered. The solid was washed with n-hexane and dried to give 15.6 g of 1-(4-chlorophenyl)-3-(dimethylamino)-2-buten-1-one as red crystals, mp 103°–105° C.

A mixture of 15.6 g of the preceding compound, 7.53 g of 3-aminopyrazole-4-carbonitrile and 150 ml of glacial acetic acid was stirred and heated at reflux for 15 minutes. The mixture went into solution and then a precipitate formed during reflux. The mixture was filtered to yield a light brown solid. The solid was triturated with aqueous saturated sodium bicarbonate until pH 7–8 was achieved, then was collected by filtration and dried to give 17.2 g of crude product. A one-gram portion of product was triturated with water and stirred for 2 hours at room temperature. The mixture was filtered and the solid was dried and gave the desired product as brown crystals, mp 285°–287° C.

EXAMPLE 16

5-Methyl-7-[3-(trifluoromethyl)phenyl]pyrazolo[1,5a]-pyrimidine-3-carbonitrile

A mixture of 20.0 g of 3-trifluoromethylacetophenone and 20 ml of N,N-dimethylacetamide dimethyl acetal was stirred and heated at reflux for 3 hours. The mixture was evaporated in vacuo to give a red solid. The solid was triturated with n-hexane and filtered. The solid was washed with n-hexane and dried to give 18.0 g of 3-(dimethylamino)-1-[3-(trifluoromethyl)phenyl]-2-buten-1-one as red crystals, mp 71°–73° C.

A mixture of 18.0 g of the preceding compound, 7.56 g of 3-aminopyrazole-4-carbonitrile and 150 ml of glacial acetic acid was stirred and heated at reflux for 16 hours. The reaction mixture was evaporated to dryness in vacuo to give yellow-white crystals. The crystals were triturated with aqueous saturated sodium bicarbonate solution, then filtered. The crystals were washed with water, then dried. The solid was dissolved in 800 ml of hot ethanol and cooled in an ice bath with scratching to induce crystallization. The product was collected by filtration and dried to give the product as pale cream crystals, mp 153°–155° C.

EXAMPLE 17

7-(3-Chlorophenyl)-6-methylpyrazolo[1,5-a]pyrimidine-3-carbonitrile

A mixture of 75.0 g of m-chloropropiophenone and 200 ml of N,N-dimethylformamide dimethyl acetal was stirred and heated at reflux for 16 hours. The mixture was evaporated in vacuo to give a black oil. The oil was subjected to Kugelrohr distillation at 0.5 mm of mercury and the fraction that boils at 110° C. was removed. The residue from the distillation was collected to give 35.0 g of 3'-chloro-3-dimethylamino-2-methylacrylophenone as a black oil.

A mixture of 25.0 g of the preceding compound, 11.88 g of 3-aminopyrazole-4-carbonitrile and 250 ml of glacial acetic acid was stirred and heated at reflux for 3 hours. The reaction mixture was evaporated to dryness in vacuo to give a dark brown solid. The solid was triturated with aqueous saturated sodium bicarbonate solution, then filtered. The solid was then triturated with methanol and filtered and gave the product of the example as white crystals, mp 206°–208° C.

EXAMPLE 18

7-(4-Chlorophenyl)-6-methylpyrazolo[1,5-a]pyrimidine-3-carbonitrile

A mixture of 50.0 g of p-chloropropiophenone and 200 ml of N,N-dimethylformamide dimethyl acetal was stirred and heated at reflux for 28 hours. The reaction mixture was evaporated in vacuo to give a yellow oil. The oil was then subjected to Kugelrohr distillation. The residual oil from the distillation was collected and triturated with hexane to provide crystals. The solid was collected by filtration and gave 21.5 g of 4'-chloro-3-dimethylamino-2-methylacrylophenone as yellow crystals, mp 45°–47° C.

A mixture of 21.5 g of the preceding compound, 10.368 g of 3-aminopyrazole-4-carbonitrile and 250 ml of glacial acetic acid was stirred and heated at reflux for 24 hours. The mixture was evaporated to dryness in vacuo to give brown crystals. The solid was triturated with saturated sodium bicarbonate solution to obtain pH 7–8 then the mixture was filtered. The solid was washed with water and dried and gave the desired product as light brown crystals, mp 154°–157° C.

EXAMPLE 19

4,5-Dihydro-7-[3-(trifluoromethyl)phenyl]pyrazolo[1,5-a]pyrimidine-3-carbonitrile To a solution of 6.0 g of 7-($\alpha,\alpha,\alpha$-trifluoro-m-tolyl)-pyrazolo[1,5-a]pyrimidine-3-carbonitrile (Ex. 3, U.S. Pat. No. 4,236,005) in 100 ml of glacial acetic acid, was added in portions, 3.0 g of sodium cyanoborohydride at room temperature under nitrogen. The mixture was stirred at room temperature for 2 hours. The precipitate was collected by filtration, washed with water, then dissolved in dichloromethane. The organic solution was neutralized with a saturated solution of sodium bicarbonate, then dried over anhydrous sodium sulfate and filtered. The filtrate was evaporated in vacuo and gave the desired product as a white solid. The product was recrystallized from isopropyl alcohol, mp 175°–177° C.

Following the general procedure of Example 19 and reacting the appropriate pyrazolo[1,5-a]pyrimidine derivative with sodium cyanoborohydride, the dihydro products of Examples 20–38, listed in Table VII, were obtained.

TABLE VII

| Ex. | Pyrazolo[1,5-a]pyrimidine Derivative | Dihydro-product | MP °C. |
|---|---|---|---|
| 20 | 7-Phenylpyrazolo[1,5-a]pyrimidine-3-carbonitrile | 4,5-Dihydro-7-phenylpyrazolo[1,5-a]pyrimidine-3-carbonitrile | 169–172 |
| 21 | 7-Phenylpyrazolo[1,5-a]pyrimidine-3-carboxylic acid, ethyl ester | 4,5-Dihydro-7-phenylpyrazolo[1,5-a]pyrimidine-3-carboxylic acid, ethyl ester | 109–111 |
| 22 | 7-[3-(Trifluoromethyl)phenyl]pyrazolo[1,5-a]pyrimidine-3-carboxylic acid, ethyl ester | 4,5-Dihydro-7-[3-(trifluoromethyl)phenyl]pyrazolo[1,5-a]pyrimidine-3-carboxylic acid, ethyl ester | 108–110 |
| 23 | 7-(m-Fluorophenyl)pyrazolo[1,5-a]pyrimidine-3-carbonitrile | 7-(3-Fluorophenyl)-4,5-dihydropyrazolo[1,5-a]pyrimidine-3-carbonitrile | 196–198 |
| 24 | 7-[3-(Trifluoromethyl)phenyl]pyrazolo[1,5-a]pyrimidine-3-carboxamide | 4,5-Dihydro-7-[3-(trifluoromethyl)phenyl]pyrazolo[1,5-a]pyrimidine-3-carboxamide | 157–160 |
| 25 | 7-(2,5-Dichlorophenyl)-2-methyl pyrazolo[1,5-a]pyrimidine-3-carboxamide | 7-(2,5-Dichlorophenyl)-4,5-dihydro-2-methylpyrazolo[1,5-a]pyrimidine-3-carboxamide | 93–96 |
| 26 | 7-Phenylpyrazolo[1,5-a]pyrimidine-3-carboxamide | 4,5-Dihydro-7-phenylpyrazolo[1,5-a]pyrimidine-3-carboxamide | 149–152 |
| 27 | 2-Methyl-7-phenylpyrazolo[1,5-a]pyrimidine-3-carboxamide | 4,5-Dihydro-2-methyl-7-phenylpyrazolo[1,5-a]pyrimidine-3-carboxamide | 275–277 |
| 28 | 7-(3-Pyridyl)pyrazolo[1,5-a]pyrimidine-3-carboxamide | 4,5-Dihydro-7-(3-pyridinyl)pyrazolo[1,5-a]pyrimidine-3-carboxamide | 182–184 |
| 29 | Phenyl[7-[3-(trifluoromethyl)phenyl]pyrazolo[1,5-a]pyrimidin-3-yl]methanone | 4,5-Dihydro-7-[3-(trifluoromethyl)phenyl]pyrazolo[1,5-a]pyrimidine-3-yl]phenylmethanone | 115–117 |
| 30 | 7-(3-Chlorophenyl)pyrazolo[1,5-a]pyrimidine-3-carbonitrile | 7-(3-Chlorophenyl)-4,5-dihydropyrazolo[1,5-a]pyrimidine-3-carbonitrile | 183–186 |
| 31 | 7-(3-Nitrophenyl)pyrazolo[1,5-a]pyrimidine-3-carbonitrile | 4,5-Dihydro-7(3-nitrophenyl)pyrazolo[1,5-a]pyrimidine-3-carbonitrile | 230–233 |
| 32 | N—[3-(3-Cyanopyrazolo]1,5-a]pyrimidin-7-yl)phenyl[-N—methylacetamide | N—[3-(3-Cyano-4,5-dihydropyrazolo-[1,5-a]pyrimidinyl-7-yl)phenyl]-N—methylacetamide | 68–71 |
| 33 | N—[3-(3-Cyanopyrazolo[1,5-a]pyrimidin-7-yl)phenyl]acetamide | N—[3-(3-Cyano-4,5-dihydropyrazolo-[1,5-a]pyrimidin-7-yl)phenylacetamide | 224–227 |
| 34 | 7-(3-Chlorophenyl)-6-methylpyrazolo-[1,5-a]pyrimidine-3-carbonitrile | 7-(3-Chlorophenyl)-4,5-dihydro-6-methylpyrazolo[1,5-a]pyrimidine-3-carbonitrile | 206–208 |
| 35 | 7-(4-Chlorophenyl)-6-methylpyrazolo-[1,5-a]pyrimidine-3-carbonitrile | 7-(4-Chlorophenyl)-4,5-dihydro-6-methylpyrazolo[1,5-a]pyrimidine-3-carbonitrile | 203–205 |
| 36 | 5-Methyl-7-[3-(trifluoromethyl)-phenyl]pyrazolo[1,5-a]pyrimidine-3-carbonitrile | 4,5-Dihydro-5-methyl-7-[3-(trifluoromethyl)phenyl]pyrazolo[1,5-a]pyrimidine-3-carbonitrile | 160–163 |
| 37 | 6-Methyl-7-[3-(trifluoromethyl)-phenyl[pyrazolo]1,5-a]pyrimidine-3-carbonitrile | 4,5-Dihydro-6-methyl-7-[3-(trifluoromethyl)phenyl]pyrazolo[1,5-a]pyrimidine-3-carbonitrile | 178–182 |
| 38 | 7-(3-Fluorophenyl)pyrazolo[1,5-a]- | 7-(3-Fluorophenyl)-4,5-dihydropyrazolo- | 122–125 |

| Ex. | Pyrazolo[1,5-a]pyrimidine Derivative | Dihydro-product | MP °C. |
|---|---|---|---|
| | pyrimidine-3-carboxamide | [1,5-a]pyrimidine-3-carboxamide | |

TABLE VII-continued

In a manner similar to the preceeding examples, the following compounds may be prepared:
4,5-Dihydro-2-methyl-7-[3-(trifluoromethyl)phenyl]-pyrazolo[1,5-a]pyrimidine-3-carbonitrile;
4,5-Dihydro-2-methyl-7-[3-(trifluoromethyl)phenyl]-pyrazolo[1,5-a]pyrimidine-3-carboxamide;
4,5-Dihydro-7-(3-methoxyphenyl)pyrazolo[1,5-a]pyrimidine-3-carbonitrile;
4,5-Dihydro-7-[2-(trifluoromethyl)phenyl]pyrazolo[1,5-a]pyrimidine-3-carbonitrile;
2-Ethyl-4,5-dihydro-6-methyl-7-[3-(trifluoromethyl)-phenyl]pyrazolo[1,5-a]pyrimidine-3-carbonitrile;
4,5-Dihydro-7-(3-tolyl)pyrazolo[1,5-a]pyrimidine-3-carboxylic acid, ethyl ester;
2-Ethyl-4,5-dihydro-7-phenylpyrazolo[1,5-a]pyrimidine-3-carbonitrile;
4,5-Dihydro-7-(3,4-xylyl)pyrazolo[1,5-a]pyrimidine-3-carboxylic acid;
4,5-Dihydro-7-(3,4-dimethoxyphenyl)pyrazolo[1,5-a]pyrimidine-3-carboxylic acid, ethyl ester;
7-(4-Ethylphenyl)-4,5-dihydropyrazolo[1,5-a]pyrimidine-3-carboxylic acid, ethyl ester;
4,5-Dihydro-7-phenylpyrazolo[1,5-a]pyrimidine-3-yl, trifluoromethyl ketone;
4,5-Dihydro-7-(3-pyridinyl)pyrazolo[1,5-a]pyrimidine-3-carbonitrile;
2-Ethyl-4,5-dihydro-7-(3-pyridinyl)pyrazolo[1,5-a]pyrimidine-3-carbonitrile;
4,5-Dihydro-7-(3-pyridinyl)pyrazolo[1,5-a]pyrimidine3-carboxylic acid, ethyl ester;
2-Ethyl-4,5-dihydro-7-(3-pyridinyl)pyrazolo[1,5-a]pyrimidine-3-carboxylic acid, ethyl ester;
4,5-Dihydro-7-(3-thienyl)pyrazolo[1,5-a]pyrimidine-3-carbonitrile;
4,5-Dihydro-2,6-dimethyl-7-(3-pyridinyl)pyrazolo[1,5-a]-pyrimidine-3-carbonitrile;
3-Chloro-2-ethyl-4,5-dihydro-7-(3-pyridinyl)pyrazolo-[1,5-a]pyrimidine;
4,5-Dihydro-7-(6-methyl-2-pyridinyl)pyrazolo[1,5-a]pyrimidine-3-carbonitrile;
4,5-Dihydro-7-[3-(trifluoromethyl)phenyl]pyrazolo[1,5-a]-pyrimidine;
3-Chloro-4,5-dihydro-7-[3-(trifluoromethyl)phenyl]-pyrazolo-[1,5-a]pyrimidine;
3-Chloro-4,5-dihydro-7-(3-pyridinyl)pyrazolo[1,5-a]pyrimidine; and the like.

EXAMPLE 39

4,5-Dihydro-4-methyl-7-[3-(trifluoromethyl)phenyl]-pyrazolo[1,5-a]pyrimidine-3-carbonitrile A mixture of 1.5 g of 4,5-dihydro-7-[3-(trifluoromethyl)phenyl]
A mixture of 1.5 g of 4,5-dihydro-7-[3-(trifluoromethyl)phenyl]pyrazolo[1,5-a]pyrimidine-3-carbonitrile (Ex. 19) and 220 mg of 60% sodium hydride dispersed in mineral oil in 50 ml of N,N-dimethylformamide was stirred at room temperature under nitrogen for 3 1/2 hours. Then one ml of iodomethane was added and the reaction mixture was stirred under nitrogen for 16 hours. The mixture was evaporated in vacuo and gave an oil. The oil crystallized upon trituration in n-hexane to give the product which was recrystallized from ethyl acetate:n-hexane (1:4) and this gave the desired product as yellow crystals, mp 120°–122° C.

EXAMPLE 40

4,5,6,7-Tetrahydro-7-[3-(trifluoromethyl)phenyl]-pyrazolo[1,5-a]pyrimidine-3-carboxamide A solution of 3.44 g of 4,5-dihydro-7-[3-(trifluoromethyl)phenyl]pyrazolo[1,5-a]pyrimidine-3-carboxamide (Ex. 24) in 40 ml of trifluoroacetic acid was stirred under nitrogen and heated to 60° C. in an oil bath. Then 5.0 ml of triethylsilane was added and the mixture was stirred at 60° C. for 24 hours. The reaction mixture was cooled and carefully poured into a beaker containing a 25% aqueous solution of potassium hydroxide and cracked ice. The product which precipitated was extracted into chloroform. The chloroform was washed with water, dried over anhydrous sodium sulfate and filtered. The filtrate was evaporated in vacuo and gave crystals which were recrystallized from toluene-hexane to give the desired product, mp 152°–154° C.

EXAMPLE 41

4,5,6,7,-Tetrahydro-7-[3-(trifluoromethyl)phenyl]-pyrazolo[1,5-a]pyrimidine-3-carbonitrile A mixture of 1.0 g of 4,5,6,7-tetrahydro-7-[3-(trifluoromethyl)phenyl]pyrazolo[1,5-a]pyrimidine-3-carboxamide, 0.44 g of potassium carbonate and 10 ml of ethyl chloroformate in 30 ml of p-dioxane was heated at reflux for 3 hours. The mixture was evaporated to dryness in vacuo. The residue was extracted with dichloromethane and the combined extracts were filtered, then evaporated and gave 0.6 g of an oil. The oil was triturated with etherhexane and gave 250 mg of a white solid. The solid was subjected to preparative thick layer chromatography, using chloroform:ethanol(10:1). The product at Rf 0.64 was collected and separated and gave the product of the example as a white solid, mp 183°–185° C.

EXAMPLE 42

Phenyl[4,5,6,7-tetrahydro-7-(4-pyridinyl)pyrazolo[1,5-a]pyrimidin-3-yl]methanone To a 20.0 g portion of phenyl[7-(4-pyridinyl)-pyrazolo[1,5-a]pyrimidin-3-yl]methanone (prepared as described in Ex. 9) suspended and stirred in 100 ml of glacial acetic acid under nitrogen was added in portions 8.5 g of sodium cyanoborohydride, during this addition another 50 ml of glacial acetic was also added. After 3 hours the solution was evaporated to dryness in vacuo. The residue was dissolved in dichloromethane and treated with saturated sodium bicarbonate until basic. The organic layer was separated and dried over anhydrous sodium sulfate. Evaporation gave a gummy solid. The solid was recrystallized from isopropyl alcohol and gave the desired product as a light yellow solid, mp 186°–189° C.

EXAMPLE 43

7-(3-Fluorophenyl)-4,5,6,7-tetrahydropyrazolo[1,5-a]pyrimidine-3-carbonitrile To a 5.0 g portion of 7-(3-fluorophenyl)-4,5-dihydropyrazolo[1,5-a]pyrimidine-3-carbonitrile (prepared as described in Ex. 23) in 50 ml of trifluoroacetic acid, stirred under nitrogen and heated to 60° C. was added 7.2 ml of triethylsilane. Heating was continued for 4 hours, then the mixture was stirred at room temperature for 16 hours. The mixture was carefully poured into an ice cooled beaker containing 150 ml of water and 40 g of potassium hydroxide. The precipitate formed was collected, washed with water and dried. The solid was dissolved in dichloromethane and filtered through hydrous magnesium silicate. Evaporation of the filtrate gave a white solid. Recrystallization from isopropyl alcohol gave the desired product, mp 146°–148° C.

EXAMPLE 44

7-(3-Chlorophenyl)-4,5,6,7-tetrahydropyrazolo[1,5-a]pyrimidine-3-carbonitrile To an 8.0 g portion of 7-(3-chlorophenyl)-4,5-dihydropyrazolo[1,5-a]pyrimidine-3-carbonitrile (prepared as described in Ex. 30) in 65 ml of trifluoroacetic acid, stirred under nitrogen and heated to 55° C. was added 7.3 ml of triethylsilane. The reaction mixture was stirred and heated at 60° C. for 7½ hours. The mixture was then carefully poured into an ice cooled beaker containing 100 ml of 25% aqueous potassium hydroxide. The precipitate which formed was collected by filtration and dissolved in chloroform. The chloroform solution was washed with saturated sodium chloride solution, dried over anhydrous sodium sulfate and filtered. The filtrate was concentrated in vacuo to give 6.8 g of white crystals. The crystals were triturated with ether. The ether was collected and crystals formed. The crystals were washed with ether and gave 2.8 g of white crystals. The crude product, 2.8 g, was chromatographed on a liquid chromatograph using a silica gel column and eluting with 5% ethyl acetate/chloroform. The fraction containing the desired product was collected and evaporated in vacuo and gave crystals, mp 148°–150° C.

EXAMPLE 45

7-(3-Chlorophenyl)-4,5,6,7,-tetrahydro-5-methylpyrazolo[1,5-a]pyrimidine-3-carbonitrile To an unweighed amount of 7-(3-chlorophenyl)-5-methylpyrazolo[1,5-a]pyrimidine-3-carbonitrile (prepared as described in Ex. 14) in a stirred mixture of one liter of tetrahydrofuran and one liter of methyl alcohol, under nitrogen was added 20.0 g of sodium borohydride, portionwise. The mixture was stirred for 8 hours at room temperature, then allowed to stand for 3 days providing two layers. The top layer was separated, dried over anhydrous sodium sulfate and filtered. The filtrate was evaporated in vacuo to give a yellow oil. The oil was dissolved in 250 ml of chloroform and filtered through hydrous magnesium silicate and evaporated to a yellow oil. The oil was triturated with ether, forming crystals on scratching. The crystals were collected to give the desired product as white crystals, mp 192°–195° C.

EXAMPLE 46

7-(4-Chlorophenyl)-4,5,6,7-tetrahydro-5-methylpyrazolo [1,5-a]pyrimidine-3-carbonitrile To a 17.2 g portion of 7-(4-chlorophenyl)-5-methylpyrazolo[1,5-a]pyrimidine-3-carbonitrile (prepared as described in Ex. 15) in a stirred mixture of one liter of tetrahydrofuran and one liter of methyl alcohol was added under nitrogen 10.0 g of sodium borohydride, portionwise. The mixture was heated to 55° C. for 6 hours, then evaporated in vacuo to give a gummy solid. The solid was triturated with ether then collected by filtration. The solid was recrystallized from 800 ml of methyl alcohol and collected by filtration to give the desired product as white crystals, mp 215°–217° C.

EXAMPLE 47

4,5,6,7-Tetrahydro-7-[3-(trifluoromethyl)phenyl]-pyrazolo[1,5-a]pyrimidine-3-carbonitrile To a stirred mixture of 14.0 g of 5-methyl-7-[3-(trifluoromethyl)phenyl]pyrazolo[1,5-alpyrimidine-3-carbonitrile (prepared as described in Ex. 16) in 250 ml of glacial acetic acid, under nitrogen was added portionwise 29.5 g of sodium cyanoborohydride. The mixture was heated at 55°–60° C. in a water bath for 16 hours then was evaporated in vacuo to give a white solid. The solid was triturated with saturated sodium bicarbonate to neutralize to pH 7–8. The crystals were collected by filtration and dissolved in 200 ml of absolute ethanol by heating on a steam bath. The solution was evaporated in vacuo and gave 10.1 g of white crystals. The crude product was chromatographed on a Waters Prep. 500A Liquid Chromatograph using a silica gel column and eluting with ethyl acetate:hexane (35:65) and collecting fractions for two peaks. The second peak fraction was evaporated in vacuo and gave the product of the example as white crystals, mp 192°–194° C.

EXAMPLE 48

4,5,6,7-Tetrahydro-7-[3-(trifluoromethyl)phenyl]-pyrazolo[1,5-a]pyrimidine-3-carbonitrile A mixture of 1.5 parts of 4,5-dihydro-7-[3-(trifluoromethyl)phenyl]pyrazolo[1,5-a]pyrimidine-3-carbonitrile, 50 parts of ethyl acetate, 10 parts of acetic acid and 0.2 parts of 5% palladium-on-carbon catalyst was shaken on a Parr hydrogenator under about 30 pounds of hydrogen pressure for 4.5 hours. The reaction mixture was filtered, and the mother liquor was concentrated to remove the solvent. The yellow oil which was obtained was crystallized by trituration in ether. The crystalline product was recrystallized from ethyl acetate by addition of hexane. The product 4,5,6,7-tetrahydro-7-[3-(trifluoromethyl)phenyl]pyrazolo[1,5-a]pyrimidine-3-carbonitrile melted at 181°–183° C.

EXAMPLE 49

4,5,6,7-Tetrahydropyrazolo[1,5-a]pyrimidine-3-carboxamide

To a stirred mixture of 4.0 g of pyrazolo[1,5-a]-pyrimidine-3-carbonitrile in 200 ml of methyl alcohol under nitrogen at, room temperature, was added, one at a time, 3 pellets of sodium borohydride. The mixture was stirred for several hours and then was allowed to stand at room temperature. The product was collected by filtration to give 1.75 g of 4,5,6,7-tetrahydropyrazolo[1,5-a]pyrimidine-3-carbonitrile, mp 206°-207° C.

The preceding product, 1.75 g, was dissolved in concentrated sulfuric acid and stirred for 16 hours. The reaction mixture was carefully poured onto ice and made slightly basic with ammonium hydroxide. The precipitate was collected by filtration to give the product of the example as colorless crystals, mp 247°-248° C.

EXAMPLE 50

4,5,6,7,-Tetrahydro-2-methylpyrazolo[1,5-a]pyrimidine-3-carbonitrile

A stirred mixture of 7.32 g of 5-amino-3-methylpyrazole-4-carbonitrile and 10.0 g of malonaldehyde bis(dimethylacetal) in 50 ml of glacial acetic acid was heated at reflux for 8 hours. The reaction mixture was cooled and evaporated in vacuo. The residue was partitioned between saturated sodium bicarbonate and dichloromethane. The organic layer was dried over anhydrous sodium sulfate and passed through hydrous magnesium silicate. The eluent was evaporated to give 7.65 g of 2-methylpyrazolo[1,5-a]pyrimidine-3-carbonitrile, mp 179°-181° C.

To a stirred mixture of 5.0 g of the preceding product and 250 ml of methyl alcohol under nitrogen was added sodium borohydride. The mixture was stirred at room temperature for several hours, then was concentrated. The residue was recrystallized from dichloromethane/n-hexane to give the desired product as colorless crystals, mp 170°-172° C.

EXAMPLE 51

4,5,6,7-Tetrahydro-2-methylpyrazolo[1,5-a]pyrimidine-3-carboxamide

A 1.0 g portion of 4,5,6,7-tetrahydro-2-methylpyrazolo[1,5-a]pyrimidine-3-carbonitrile was dissolved with stirring in 5.0 ml of concentrated sulfuric acid. The mixture was stirred for 6 hours at room temperature then poured onto ice. This mixture was made basic with concentrated ammonium hydroxide and then was filtered to give the product of the example as a colorless solid, mp 234°-236° C.

EXAMPLE 52

4,5,6,7-Tetrahydro-2-methyl-5,7-dipropylpyrazolo[1,5-a]pyrimidine-3-carbonitrile A stirred mixture of 4.88 g of 5-amino-3-methylpyrazole-4-carbonitrile and 6.25 g of 4,6-nonanedione in 50 ml of glacial acetic acid was heated at reflux for 10 hours. The reaction mixture after reflux was worked up as described in Example 50 to give 7.80 of 2-methyl-5,7-dipropylpyrazolo[1,5-a]pyrimidine-3-carbonitrile, mp 73°-74° C.

To a 2.0 g portion of the preceding compound in 80 ml of methyl alcohol under nitrogen was added 0.33 g of sodium borohydride, portionwise, while the solution was stirred. After one hour the solvent was evaporated and the residue was partitioned between saturated sodium bicarbonate and dichloromethane and purified as hereinabove described to give the product of the example, mp 98°-99° C.

EXAMPLE 53

4,5,6,7-Tetrahydropyrazolo[1,5-a]pyrimidine-3-carboxylic acid, ethyl ester

A stirred mixture of 10.88 g of 5-amino-4-pyrazolecarboxylic acid, ethyl ester, 11.51 g of malonaldehyde bis(dimethyl acetal) and 100 ml of glacial acetic acid was heated at reflux for 16 hours, then worked up as described in Example 50 to give 7.8 g of pyrazolo[1,5-a]pyrimidine-3-carboxylic acid, ethyl ester.

To a stirred mixture of 5.0 g of the preceding product in 200 ml of ethyl alcohol plus 100 ml of methyl alcohol, under nitrogen at room temperature was added about 1.0 g of sodium borohydride, portionwise. The reaction mixture was stirred for 16 hours and then was evaporated in vacuo. The residue was partitioned between saturated sodium bicarbonate solution and dichloromethane. The organic layer was passed through a short column of hydrous magnesium silicate and n-hexane was added to the eluent to crystallize the product. Recrystallization from dichloromethane/hexane gave the desired product, mp 158°-159° C.

EXAMPLE 54

Phenyl(4,5,6,7-tetrahydropyrazolo[1,5-a]pyrimidin-3-yl)methanone

A mixture of 1.87 g of (3-amino-1H-pyrazol-4-yl)phenylmethanone (prepared as described in U.S. Patent application Ser. No. 612,811, filed May 24, 1984), 1.64 g of malonaldehyde bis(dimethyl acetal) and 25 ml of glacial acetic acid was heated at reflux for 6 hours. The solvent was evaporated and the solid was worked up as described in Example 50 and gave 1.70 g of phenylpyrazolo[1,5-a]pyrimidin-3-yl-methanone, mp 174°-175° C.

A mixture of 3.07 g of the preceding compound (prepared in the manner described above), 60 ml of N,N-dimethylformamide and 600 mg of 10% palladium-on-carbon catalyst was hydrogenated with an initial pressure of 15 lbs. of hydrogen until no additional hydrogen was absorbed. The resulting mixture was filtered to remove the catalyst and then evaporated to dryness. The crude product was partitioned between dichloromethane and saturated aqueous sodium bicarbonate solution and after separation, the organic layer was dried over anhydrous sodium sulfate and passed through a short column of hydrous magnesium silicate. The eluent was refluxed on a steam bath, with the gradual addition of n-hexane. When crystallization was noted, the solution was cooled and the solid was collected by filtration to give the desired product, mp 173°-174° C.

EXAMPLE 55

2-Furanyl(4,5,6,7-tetrahydropyrazolo[1,5-a]pyrimidin-3-yl)-methanone

A mixture of 7.08 g of (3-amino-1H-pyrazol-4-yl)-2-furanylmethanone (prepared as described in U.S. Pat. appliction Ser. No. 612,811, filed May 24, 1984), 8.20 g of malonaldehyde bis(dimethyl acetal) and 100 ml of glacial acetic acid was heated at reflux for 8 hours. The solvent was evaporated and the solid was worked up as described in Example 50 to give 4.92 g of 2-furanylpyrazolo[1,5-a]pyrimidin-3-yl-methanone, mp 222°-224° C.

A mixture of 1.0 g of the preceding compound, 100 ml of N,N-dimethylformamide and 500 mg of 10% palladium-on-carbon catalyst was hydrogenated and isolated as described in Example 54 to obtain 2-furanyl(4,5,6,7-tetrahydropyrazolo[1,5-a]pyrimidin-3-yl)methanone, mp 138°–139° C.

EXAMPLE 56

2,2-Dimethyl-1-(4,5,6,7-tetrahydropyrazolo[1,5-a]pyrimidin-3-yl)-1-propanone

A mixture of 25.0 g of pivaloyl acetonitrile in 50 ml of N,N-dimethylformamide dimethyl acetal was stirred at room temperature for 8 hours under argon and then the solvent was evaporated and n-hexane was added with stirring. The product was collected by filtration to give 34.6 g of 2-[(dimethylamino)methylene]-4,4-dimethyl-3-oxopentanenitrile.

A mixture of 18.0 g of the preceding product, 15.0 g of aminoguanidine nitrate, 250 ml of ethyl alcohol and 11.0 ml of 10N sodium hydroxide was heated at reflux for 8 hours. The solvent was evaporated and water was added to yield an oily precipitate which crystallized with scratching. The precipitate was partitioned between saturated sodium bicarbonate and dichloromethane and worked up as described in Example 50 to give 9.68 g of product. A 1.33 g amount of this material was recrystallized from dichloromethane/hexane to give 1.02 g of 1-(3-amino-1H-pyrazol-4-yl)-2,2-dimethyl-1-propanone, mp 159°–160° C.

A stirred mixture of 3.34 g of the preceding product (prepared in the manner described above), 3.50 g of malonaldehyde bis(dimethyl acetal) and 100 ml of glacial acetic acid was heated at reflux for 8 hours. The reaction mixture was cooled and evaporated in vacuo and then partitioned and worked up as described hereinabove to give 3.19 g of 2,2-dimethyl-1-pyrazolo[1,5-a]pyrimidin-3-yl-1-propanone, mp 130°–131° C.

A mixture of 2.0 g of the preceding compound, 40 ml of N,N-dimethylformamide and 400 mg of 10% palladiumon-carbon catalyst was hydrogenated and isolated as described in Example 54 to obtain the compound 2,2-dimethyl-1(4,5,6,7-tetrahydropyrazolo[1,5-a]pyrimidin-3-yl)-1-propanone, mp 169°–170° C.

EXAMPLE 57

4,5-Dihydro-7-[3-(trifluoromethyl)phenyl]pyrazolo[1,5-a]pyrimidine-3-carboxylic acid A 3.37 g amount of 4,5-dihydro-7-[3-(trifluoromethyl)phenyl]pyrazolo[1,5-a]pyrimidine-3-carboxylic acid, ethyl ester (prepared as described in Ex. 22) was added to a solution of 1.4 g of potassium hydroxide in 100 ml of ethanol. This mixture was heated at reflux for 5 hours, cooled to room temperature and evaporated to dryness in vacuo. The residue was dissolved in water and the solution was neutralized to pH 7.0 with concentrated hydrochloric acid. The white precipitate formed was collected by filtration, washed with water and dried in vacuo to give 2.5 g of the desired product as a whtie solid, mp 175°–177° C.

EXAMPLE 58

7-(2,5-Dichlorophenyl)-4,5-dihydropyrazolo[1,5-a]pyrimidine-3-carbonitrile

A mixture of 98.3 g of 2',5'-dichloro-3-dimethylaminoacrylophenone and 43.5 g of 3-aminopyrazole-4-carbonitrile in one liter of glacial acetic acid was heated at reflux for 6¾ hours. The reaction mixture was cooled and diluted with water to provide a precipitate which was collected, washed with water and dried in vacuo to give 107.6 g of 7-(2,5-dichlorophenyl)pyrazolo[1,5-a]pyrimidine-3-carbonitrile as pale yellow crystals, mp 202°–204° C.

To a stirred mixture of 59.7 g of the preceding product in 600 ml of glacial acetic acid, under nitrogen was added portionwise about half of 25.9 g of sodium cyanoborohydride. The mixture was then warmed on a steam bath with continued stirring until solution occured. The heat was removed and the remainder of the sodium cyanoborohydride was added under nitrogen and the reaction mixture was stirred for an additional 2½ hours. The yellow precipitate that formed was collected by filtration and washed with water and then neutralized by washing with a saturated solution of sodium bicarbonate. The precipitate was dried in vacuo to give 41.1 g of the product of the example as a light yellow solid, mp 222°–223° C.

EXAMPLE 59

7-(4-Chlorophenyl)-4,5-dihydropyrazolo[1,5-a]pyrimidine-3-carbonitrile

A mixture of 87.0 g of 4'-chloro-3-dimethylaminoacrylophenone and 44.9 g of 3-aminopyrazole-4-carbonitrile in 500 ml of glacial acetic acid was heated at reflux for 5½ hours and then the precipitated product was collected by filtration, washed with water and dried to give 87.7 g of solid. The above filtrate was diluted with water to precipitate additional 13.6 g of solid. The combined product 101.3 g was combined with one liter of absolute ethanol and was heated to boiling and then the mixture was filtered hot to give 79.7 g of 7-(4-chlorophenyl)pyrazolo[1,5-a]pyrimidine-3-carbonitrile, mp 244°–245° C.

To a stirred mixture of 46.8 g of 7-(4-chlorophenyl)-pyrazolo[1,5-a]pyrimidine-3-carbonitrile in 1.2 liters of glacial acetic acid under nitrogen and heated on a steam bath was added portionwise 30.0 g of sodium cyanoborohydride, heating and stirring was continued until all the solid was dissolved. The heat was removed and stirring was continued. A solid mass formed and was collected by filtration. The solid was washed with water, then with aqueous ammonia, followed by water again. The solid was dried in vacuo to give 29.1 g of the product of the example as a white solid, mp 208°–209° C.

EXAMPLE 60

3-Chloro-4,5-dihydro-7-[3-(trifluoromethyl)phenyl-pyrazolo[1,5-a]pyrimidine

To a stirred mixture of 13.3 g of 3-chloro-7-[3-(trifluoromethyl)phenyl]pyrazolo[1,5-a]pyrimidine in 150 ml of glacial acetic acid, under nitrogen at room temperature was added portionwise 7.02 g of sodium cyanoborohydride. The mixture was stirred for 24 hours then was evaporated in vacuo to give an oil. The oil was dissolved in dichloromethane and washed with saturated sodium bicarbonate. The organic layer was separated, dried over anhydrous sodium sulfate, filtered and the filtrate was evaporated in vacuo to give an oil which was then triturated with hexane. The crystals that formed were collected by filtration to give 6.7 g of the desired product as yellow crystals, mp 89°–92° C.

EXAMPLE 61

4,5-Dihydro-7-[3-(trifluoromethyl)phenyl]pyrazolo[1,5-a]pyrimidine

To a stirred mixture of 25.0 g of 7-[3-(trifluoromethyl)phenyl]pyrazolo[1,5-a]pyrimidine in 250 ml of glacial acetic acid, at room temperature, under nitrogen was added portionwise 14.92 g of sodium cyanoborohydride. The resultant solution was stirred for 24 hours, and then was evaporated in vacuo to give an oil. The oil was dissolved in chloroform and washed with saturated sodium bicarbonate. The organic layer was separated, dried over anhydrous sodium sulfate and filtered. The filtrate was evaporated in vacuo to give a semi-solid which was chromatographed on a silica gel column using a mixture of 25% ethyl acetate and 75% hexane as the solvent system. The product fraction was collected and evaporated to give 6.2 g of the desired product as orange crystals, mp 61°–64° C.

EXAMPLE 62

7-(2,5-Dichlorophenyl)-4,5,6,7-tetrahydro-6-methylpyrazolo[1,5-a]pyrimidine-3-carbonitrile A mixture of 50.0 g of 2,5-dichloroacetophenone and 50 ml of N,N-dimethylacetamide dimethyl acetal was stirred and heated at reflux for 12½ hours. The mixture was then cooled and evaporated in vacuo to give an oil which crystallized on scratching to give a dark red solid. This was collected and washed with hexane/ether to give 58.8 g of 1-(2,5-dichlorophenyl)-3-(dimethylamino)-2-buten-1-one as a red solid.

A mixture of 58.8 g of the preceding product and 24.5 g of 3-aminopyrazole-4-carbonitrile in 400 ml of glacial acetic acid was heated at reflux for about 5 hours. The reaction mixture was cooled and was diluted with water and the precipitate that formed was collected by filtration. This was washed several times with water and dried to give 68.5 g of 7-(2,5-dichlorophenyl)-5-methylpyrazolo[1,5-a]pyrimidine-3-carbonitrile as a light yellow solid, mp 229°–230° C.

To a stirred mixture of 68.5 g of the above product in one liter of glacial acetic acid warmed on a steam bath was added, under nitrogen, portionwise, 28.4 g of sodium cyanoborohydride. Heating and stirring was continued for about 6 hours, then an additional 21.6 g of sodium cyanoborohydride was added and stirring and heating was continued for 5½ hours. The reaction mixture was filtered hot to remove insoluble material totaling 23.1 g (A). The filtrate was cooled in an ice bath to crystallize a solid which was collected by filtration and washed with water to yield 21.9 g (B). The filtrate from (B) was diluted with water to give an additional precipitate which was collected after standing and gave 19.07 g (C).

A mixture comprised of 10.0 g of (A), 10.0 g of (B) and 10.0 g of (C) was stirred in 150 ml of methanol and 500 ml of tetrahydrofuran, under nitrogen and then 12.44 g of sodium borohydride was added portionwise. The mixture was heated under reflux for 7 hours and then filtered hot. The filtrate was cooled to room temperature and water was added to separate and oil which was extracted into chloroform. The organic layer was separated, dried over anhydrous sodium sulfate and filtered. The filtrate was evaporated in vacuo to give an off-white solid which was triturated with ether/hexane to give 19.4 g of the product of the example as a white solid, mp 184°–185° C.

EXAMPLE 63

7-(3,4-Dichlorophenyl)-4,5-dihydropyrazolo[1,5-a]pyrimidine-3-carbonitrile

A mixture of 50.0 g of 3,4-dichloroacetophenone and 75 ml of N,N-dimethylformamide dimethyl acetal was heated under reflux for 6 hours, then allowed to cool for 16 hours. The crystalline precipitate was collected by filtration, washed with hexane and dried. The addition of hexane to the above filtrate precipitated some additional product which was collected by filtration. The precipitates were combined, washed with hexane and dried in vacuo to give 55.0 g of 3',4'-dichloro-3-dimethylaminoacrylophenone as bright yellow crystals.

A mixture of 55.0 g of the preceding product and 24.3 g of 3-aminopyrazole-4-carbonitrile in 500 ml of glacial acetic acid was heated at reflux for 5 hours. The reaction mixture was allowed to stand at room temperature for 16 hours. The solid that separated was collected by filtration, washed with water, then aqueous ammonia, followed by additional water. The product was dried in vacuo to give 62.5 g of 7-(3,4-dichlorophenyl)-pyrazolo[1,5-a]pyrimidine-3-carbonitrile as light yellow crystals.

A 25.0 g portion of the preceding product was then combined with one liter of acetic acid and to this mixture was added excess sodium cyanoborohydride in portions. The mixture was stirred for two days under nitrogen while the temperature was maintained by a steam bath. The solid that precipitated from solution was recrystallized from ethanol to give 12.0 g of 7-(3,4-dichlorophenyl)-4,5-dihydropyrazolo[1,5-a]pyrimidine-3-carbonitrile as a light yellow solid, mp 254°–256° C.

We claim:

1. A compound of the formula:

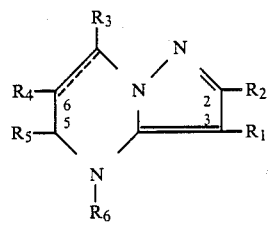

Ia or Ib wherein—represents the presence of a double bond between the $C_6$ and $C_7$ position, Ia, or the absence of a double bond between the $C_6$ and $C_7$ position, Ib; $R_1$ is hydrogen, bromo, chloro, carbamoyl, carboxyl, carboxyalkoxyl where alkoxyl is ($C_1$-$C_3$), cyano, —CO—CF$_3$, COONa,

—CO—C(CH$_3$)$_3$, or

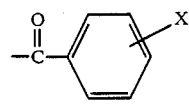

where X is hydrogen, cyano, halogen or nitro; $R_2$, $R_4$ and $R_5$ are hydrogen or lower alkyl($C_1$–$C_3$); $R_3$ is hydrogen, alkyl($C_1$–$C_3$),

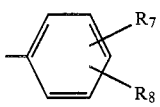

where $R_7$ and $R_8$ may be the same or different and are hydrogen, halogen, alkyl ($C_1$–$C_3$), nitro, alkoxy($C_1$–$C_3$), trifluoromethyl, acetylamino or N-alkylacetylamino where alkyl is ($C_1$–$C_3$), and $R_3$ is also 3-thienyl, 2-pyridinyl, 3-pyridinyl or 4-pyrindinyl, either of said pyridinyl radicals being optionally substituted with an alkyl radical $R_9$, where alkyl is ($C_1$–$C_4$), and the structures of the monovalent 2-pyridinyl, 3-pyridinyl and 4-pyridinyl moieties are depicted respectively as:

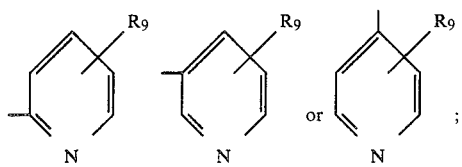

and $R_6$ is hydrogen or alkyl($C_1$–$C_3$).

2. The compound according to claim 1, 4,5-dihydro-7-[3-(trifluoromethyl)phenyl]pyrazolo[1,5-a]pyrimidine-3-carbonitrile.

3. The compound according to claim 1, 4,5-dihydro-7-phenylpyrazolo[1,5-a]pyrimidine-3-carboxamide.

4. The compound according to claim 1, 4,5-dihydro-7-[3-(trifluoromethyl)phenyl]pyrazolo[1,5-a]pyrimidine-3-carboxamide.

5. The compound according to claim 1, 4,5-dihydro-6-methyl-7-[3-(trifluoromethyl)phenyl]pyrazolo[1,5-a]pyrimidine-3-carbonitrile.

6. The compound according to claim 1, 7-(2,5-dichlorophenyl)-4,5-dihydro-2-methylpyrazolo[1,5-a]pyrimidine-3-carboxamide.

7. The compound according to claim 1, 7-(3-chlorophenyl)-4,5,6,7-tetrahydro-5-methylpyrazolo[1,5-a]pyrimidine-3-carbonitrile.

8. The compound according to claim 1, 7-(4-chlorophenyl)-4,5,6,7-tetrahydro-5-methylpyrazolo[1,5-a]pyrimidine-3-carbonitrile.

9. The compound according to claim 1, [4,5-dihydro-7-[3-(trifluoromethyl)phenyl]pyrazolo[1,5-a]pyrimidin-3-yl]phenylmethanone.

10. The compound according to claim 1, phenyl[4,5,6,7-tetrahydro-7-(4-pyridinyl)pyrazolo[1,5-a]pyrimidin-3-yl]methanone.

11. The compound according to claim 1, 4,5,6,7-tetrahydro-7-[3-(trifluoromethyl)phenyl]pyrazolo[1,5-a]pyrimidine-3-carbonitrile.

12. The compound according to claim 1, 4,5-dihydro-4-methyl-7-[3-(trifluoromethyl)phenyl]pyrazol [1,5-a]pyrimidine-3-carbonitrile.

13. The compound according to claim 1, 4,5,6,7-tetrahydropyrazolo[1,5-a]pyrimidine-3-carboxamide.

14. The compound according to claim 1, 7-(3chlorophenyl)-4,5-dihydro-6-methylpyrazolo[1,5-a]pyrimidine-3-carbonitrile.

15. A therapeutic composition of matter in dosage unit form for the treatment of hypertension which comprises 5 to 200 mg of a compound of claim 1 in association with a pharmaceutically acceptable carrier or diluent.

* * * * *